US008641604B2

(12) United States Patent  (10) Patent No.: US 8,641,604 B2
Golden et al.  (45) Date of Patent: Feb. 4, 2014

(54) STEERING SYSTEM WITH LOCKING MECHANISM

(75) Inventors: John Golden, Norton, MA (US); Mark Monroe, Osterville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 537 days.

(21) Appl. No.: 12/464,770

(22) Filed: May 12, 2009

(65) Prior Publication Data

US 2009/0287188 A1 Nov. 19, 2009

Related U.S. Application Data

(60) Provisional application No. 61/052,966, filed on May 13, 2008.

(51) Int. Cl.
*A61B 1/00* (2006.01)
*A61M 31/00* (2006.01)
*A61M 37/00* (2006.01)
*A61M 25/00* (2006.01)

(52) U.S. Cl.
USPC ........... 600/148; 600/101; 600/139; 600/146; 604/95.04; 604/528

(58) Field of Classification Search
USPC .................. 600/585, 139, 141, 146–149; 604/95.04, 528
See application file for complete search history.

(56) References Cited

U.S. PATENT DOCUMENTS

| 4,461,282 | A | * | 7/1984 | Ouchi et al. | 600/148 |
| 4,742,816 | A | * | 5/1988 | Suzuki et al. | 600/134 |
| 5,014,685 | A | * | 5/1991 | Takahashi | 600/148 |
| 5,507,717 | A | * | 4/1996 | Kura et al. | 600/146 |
| 5,634,466 | A | | 6/1997 | Gruner | |
| 2001/0037051 | A1 | | 11/2001 | Fujii et al. | |
| 2002/0062063 | A1 | | 5/2002 | Ogura et al. | |
| 2008/0021277 | A1 | | 1/2008 | Stefanchik et al. | |

OTHER PUBLICATIONS

Written Opinion of the International Searching Authority, dated Nov. 11, 2009, in related application PCT/US2009/043647.
International Search Report, dated Nov. 11, 2009, in related application PCT/US2009/043647.

* cited by examiner

*Primary Examiner* — Brian Szmal
*Assistant Examiner* — Megan Leedy
(74) *Attorney, Agent, or Firm* — Bookoff McAndrews, PLLC

(57) ABSTRACT

A steerable device, such as a steerable catheter, may include a control handle and an insertion shaft extending outwardly therefrom. In use, the insertion shaft is navigated to an area of interest for examination and/or treatment thereof. The steerable device may include a steering system that controls the deflection angle of the distal end of the insertion shaft in two or more non-planar directions for navigating the insertion shaft to the area of interest. The steering system may also include a locking mechanism for arresting or partially arresting the movement of the distal end of the insertion shaft in a first direction independent of arresting or partially arresting the movement of the distal end in a second non-planar direction.

25 Claims, 8 Drawing Sheets

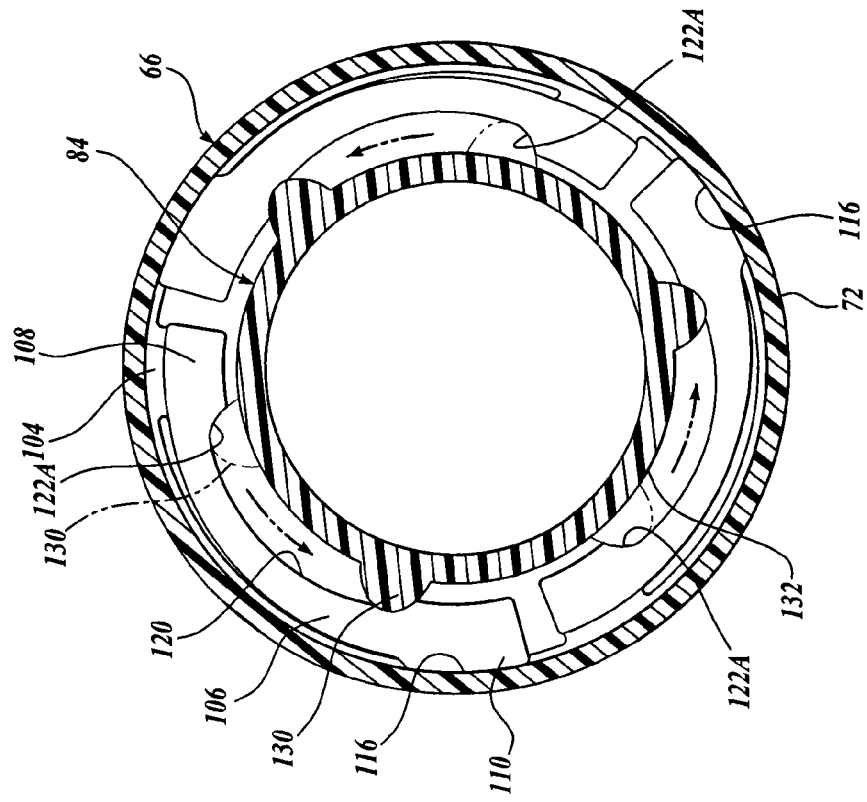
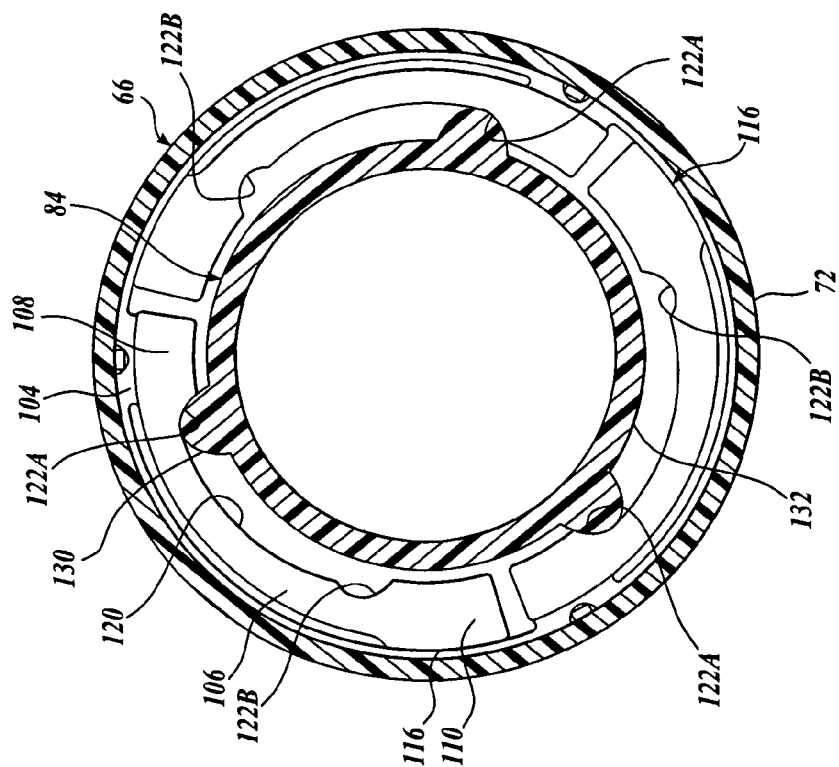
Fig. 7A.
Fig. 7B.

STEERING SYSTEM WITH LOCKING MECHANISM

CROSS-REFERENCE TO RELATED APPLICATION

This application claims the benefit of U.S. Provisional Application No. 61/052,966, filed May 13, 2008, the disclosure of which is hereby expressly incorporated by reference.

BACKGROUND

Current medical devices, such as catheters and endoscopes, are employed for the examination and/or treatment of the mammalian body. In particular, various surgical procedures employ a catheter or an endoscope to exam remote parts of the body and/or introduce surgical tools, fluids or other materials into the body for treatment thereof. For example, in some procedures, catheters and endoscopes may be used for the introduction of items including but not limited to radiographic contrast materials, drugs, angioplasty balloons, stents, fiber optic scopes, laser lights, and cutting instruments (e.g., biopsy forceps, RF cutters, atherectomy devices, etc.), into vessels, cavities, passageways, or tissues of the body.

Navigation of the catheter or endoscope through the vessels, cavities, or passageways of the body to the area of interest is critical to the success of the examination and/or treatment. To this end, modern catheters and endoscopes include an arrangement that allows the operator to deflect the distal end of an associated insertion shaft for guiding the insertion shaft through the passageways, vessels, etc., to the area of interest. For example, conventional steerable catheters and endoscopes typically comprise a control handle from which an elongated insertion shaft extends. The elongated insertion shaft is formed of a material or materials of such a stiffness so as to normally maintain the elongated shaft in a straight condition in the absence of an external force. The outer end portion of the elongated shaft is relatively flexible to permit deflection. Pairs of guide wires, also known as steering wires, are connected to the control handle, extend outwardly through the elongated shaft, and terminate at the flexible outer end portion of the elongated shaft. A guide wire control mechanism is carried by the control handle and includes a pair of rotatable control knobs that cooperate with the respective pairs of guide wires for manually controlling the angular attitude of the flexible outer end portion of the elongated tube to thereby effectively "steer" the catheter or endoscope in the up/down and right/left directions.

It is also known in the pertinent art to provide the steerable catheter or endoscope with a locking mechanism for arresting the relative deflection of the elongated shaft during use. In a conventional manner, the control knobs are manually operated to articulate the elongated shaft in four (4) directions for navigation through a vessel, cavity, or passageway of a patient. Manual release of the control knobs returns the elongated shaft to its straight condition due to the stiffness of the elongated shaft. At certain points during any particular surgical procedure, it may be desired to arrest the relative orientation of the elongated shaft. At such time, the conventional locking mechanism is activated and movement of both control knobs relative to the remainder of the catheter is simultaneously precluded. For one example of such a locking mechanism, please see co-pending application Ser. No. 11/089,380, filed Mar. 23, 2005, which is hereby expressly incorporated by reference.

While these known locking mechanisms for steerable catheters and endoscopes have proven to be acceptable for their intended applications, they are all associated with limitations. For example, it may be desirable to accomplish small positional adjustments of the elongated shaft by allowing only one control knob to effect bending at one time while the other knob is locked against rotation. Heretofore locking mechanisms, however, utilize a single locking lever to simultaneously arrest the movement of the both control knobs.

Embodiments of the present invention are directed to steering systems, and in particular, to locking mechanisms that address these limitations.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with aspects of the present invention, a steering system is provided for a steerable device having a deflectable insertion shaft through which at least first and second steering wires are routed. The steering system comprises first and second drive members adapted to be coupled to the first and second steering wires for effecting movement of the first and second steering wires, respectively. The steering system also comprises a first lock member associated with the first drive member. The first lock member is movable between an unlocked position, wherein the first drive member is movable to effect movement on the first steering wire, and a locked position, wherein the first drive member is prohibited from effecting movement on the first steering wire. The steering system further comprises a second lock member associated with the second drive member and movable independently of the first lock member. The second lock member is movable between an unlocked position, wherein the second drive member is freely movable to effect movement on the second steering wire, and a locked position, wherein the second drive member is prohibited from effecting movement on the second steering wire.

In accordance with another aspect of the present invention, a steering system is provided for a steerable device. The steering system comprises first and second steering wires, first and second drive members coupled to the first and second steering wires for selectively tensioning the first and second steering wires, respectively, and first and second lock members independently movable between unlocked positions, wherein the first and second steering wires are freely movable, and one or more positions that either restrict or resist movement of the first and second steering wires.

In accordance with another aspect of the present invention, a control handle of a steering device is provided. The control handle comprises a handle housing adapted for connection to a deflectable insertion shaft and a steering system carried by the handle housing. The steering system comprises first and second drive members adapted for connection to the ends of first and second steering wires and a locking mechanism that locks the movement of the first drive member independently of the second drive member and locks the movement of the second drive member independently of the first drive member.

In accordance with another aspect of the present invention, a steerable device is provided. The steerable device comprises an elongated shaft having proximal and distal ends, and a deflectable distal region. The steerable device also comprises a control handle functionally coupled to the proximal end of the elongated shaft and a steering system carried by the control handle. The steering system is coupled to the distal end of the insertion shaft for deflecting the distal end about the deflectable distal region in at least first and second non-planar directions. The steerable device further comprises a locking mechanism that locks the distal end of the insertion shaft against movement in the first direction independently of locking the distal end against movement in the second direction.

In accordance with another aspect of the present invention, a steerable device is provided. The steerable device comprises an elongated shaft having proximal and distal ends, and a deflectable distal region, a control handle functionally coupled to the proximal end of the elongated shaft, and a steering system carried by the control handle and coupled to the distal end of the insertion shaft for deflecting the distal end about the deflectable distal region in at least first and second non planar directions. The steerable device further includes means for resisting or prohibiting movement of the distal end of the insertion shaft in the first direction while allowing continued deflection of the distal end of the insertion shaft in the second direction.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 7A and 7B are views depicting a cam member in an unlocked position and a locked position, respectively.

DETAILED DESCRIPTION

Embodiments of the present invention will now be described with reference to the drawings where like numerals correspond to like elements. Embodiments of the present invention are generally directed to steerable devices of the type having a control handle and a deflectable insertion shaft that is inserted into a conduit, passageway, body lumen, etc. Several embodiments of the present invention are generally directed to steering systems employed by the steerable devices for controlling the deflection of the insertion shaft, and in particular, to steering systems that comprise a locking mechanism for locking the distal end of the insertion shaft at a desired deflection angle. Embodiments of the present invention may also be directed to control handles that employ such steering systems.

Although exemplary embodiments of the present invention will be described hereinafter with reference to a steerable catheter, it will be appreciated that aspects of the present invention have wide application, and therefore, may be suitable for use with many types of medical devices, such as endoscopes (e.g., ureteroscopes, duodenoscopes), steerable fiberscopes, steerable guidewires, etc., and non-medical devices, such as borescopes. Accordingly, the following descriptions and illustrations herein should be considered illustrative in nature, and thus, not limiting the scope of the present invention, as claimed.

Figure 1:
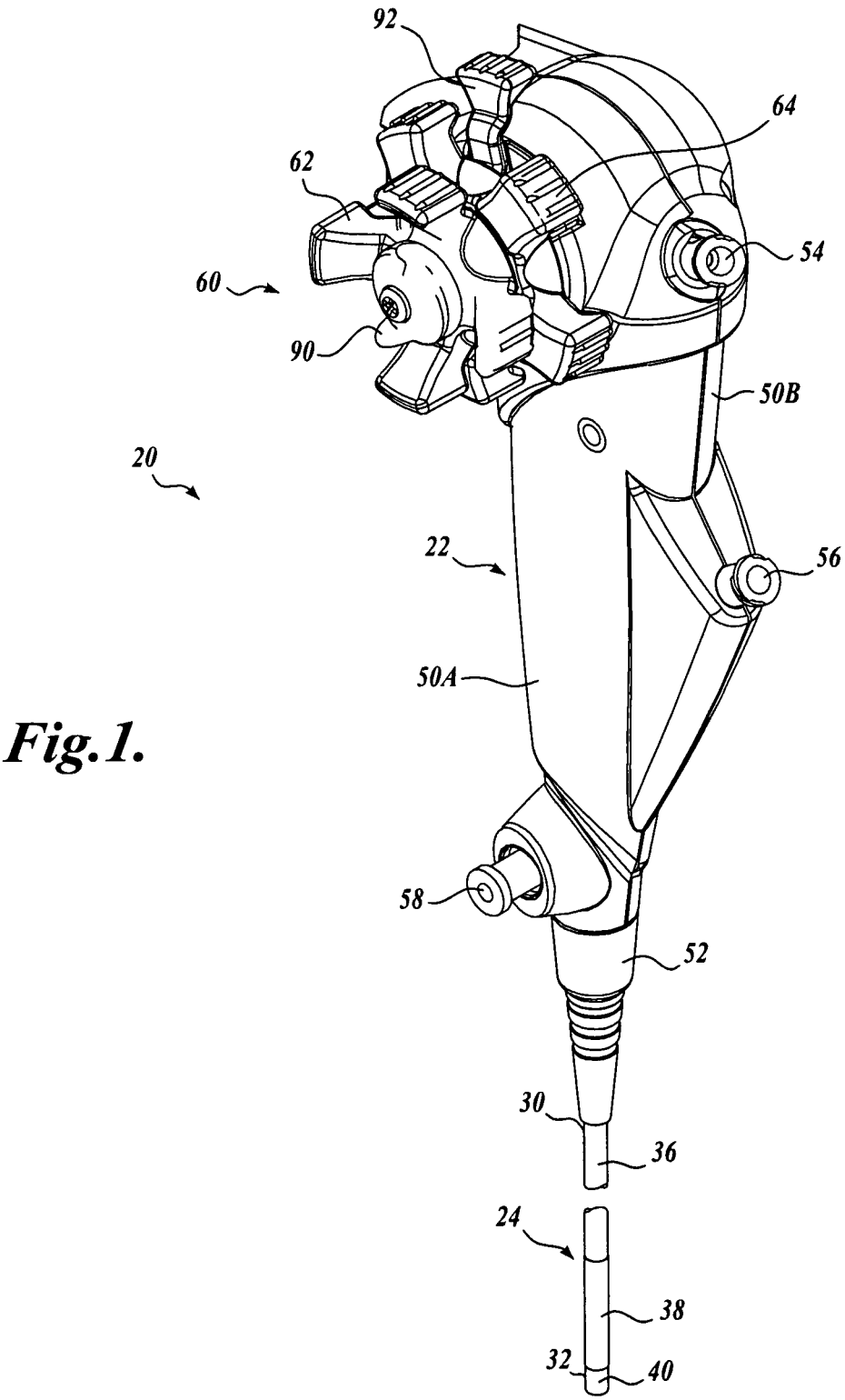
FIG. 1 is a perspective view of one embodiment of a steerable device constructed in accordance with aspects of the present invention.

With reference to FIGS. 1-7, there is shown one embodiment of a steerable device, such as a steerable catheter 20, formed in accordance with aspects of the present invention. As best shown in the embodiment of FIG. 1, the steerable catheter 20 generally includes a control handle 22 and an insertion shaft 24 extending outwardly therefrom. In use, the insertion shaft 24 is navigated through vessels, cavities, passageways, or tissues of a mammalian body to an area of interest for examination and/or treatment thereof. It will be appreciated that the steerable catheter 20 may be capable of introducing items, including but not limited to radiographic contrast materials, drugs, angioplasty balloons, stents, fiber optic scopes, laser lights, cutting instruments (e.g., biopsy forceps, RF cutters, atherectomy devices, etc.), and other endoscopic and medical devices (e.g., aspiration and infusion catheters, stone baskets, needles, cytology brushes, snares, ablation devices, etc.) to the area of interest.

As will be described in more detail below, the steerable catheter 20 includes a steering system that controls the deflection angle of the distal end of the insertion shaft 24 in two or more non-planar directions for navigating the insertion shaft 24 through the body lumens, passageways, etc., to the area of interest. As will be further described in detail below, embodiments of the steering system may also include an exemplary locking mechanism for arresting the movement of the distal end of the insertion shaft in a first direction independent of arresting the movement of the distal end in a second non-planar direction.

As best shown in FIG. 1, the insertion shaft 24 can be formed as an elongated body having a proximal end 30 and a distal end 32. The insertion shaft 24 may be formed as a hollow tube, a multi-lumen extruded shaft as shown in the cross sectional view of FIG. 2, or other structures that permit passage of a plurality of steering wires and optional instruments, such as biopsy forceps, vision probes, cutters, etc., to the distal end 32. In one embodiment, the insertion shaft 24 is cylindrical with an outer diameter between approximately 4 and 15 French, although other diameters may be used. The insertion shaft 24 may be constructed using various techniques from any suitable material, such as PEBA® (polyether block amides), nylon, polytetrafluoroethylene (PTFE), polyethylene, polyurethane, fluorinated ethylene propylene (FEP), thermoplastic polyurethane, thermoplastic elastomers and the like, or combinations and blends thereof.

The insertion shaft 24 is configured so that it is capable of being deflected or "steered" through or within the cavities, vessels, passageways, etc. of a body to an area of interest. To that end, the insertion shaft 24 can be constructed so that it varies in stiffness between the proximal end 30 and the distal end 32. In particular, the distal region of the insertion shaft 24 can be constructed to be more flexible than the proximal region. This may allow the insertion shaft 24 to be easily advanced without compressing and with minimal twisting while providing deflection capabilities for deflecting the distal end 32. In some embodiments, the flexibility may be varied gradually (e.g., increasingly) throughout the length of the insertion shaft from its proximal end 30 to its distal end 32. In other embodiments, the distal region of the insertion shaft (e.g., the most distal 1-3 inches of the insertion shaft) can be made more flexible (i.e., less stiff) than the remainder of the insertion shaft.

In the embodiment shown in FIG. 1, the insertion shaft 24 is comprised of a proximal section 36, a more flexible deflection section 38 positioned distally of the proximal section 36, and a distal tip 40 located at the distal end 32. In some embodiments, the deflectable section 38 is constructed of a material with less stiffness than the proximal section 36. In yet other embodiments, the deflection section 38 may be an articulating joint. For example, the deflection section 38 may include a plurality of segments that allow the distal end to deflect in two or more non-planar directions. For examples of articulation joints that may be practiced with embodiments of the present invention, please see co-pending U.S. patent application Ser. Nos. 10/306,149, 10/811,781, and 10/956,007, the disclosures of which are hereby incorporated by reference.

Figure 2:
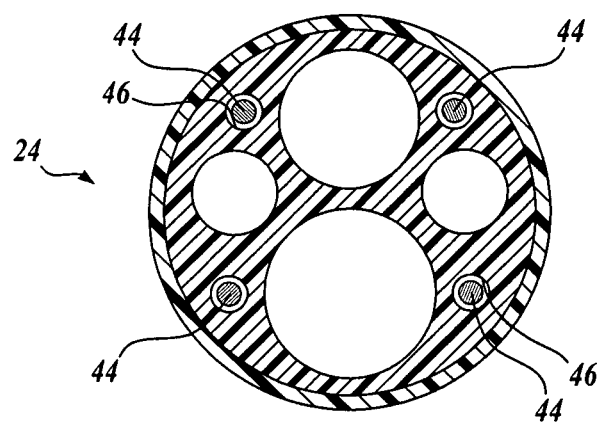
FIG. 2 is a cross sectional view of one embodiment of an insertion shaft of the steerable device of FIG. 1.

Referring now to FIGS. 1 and 2, the steerable catheter 20 further includes a plurality of steering wires 44 that cause the distal end 32 of the insertion shaft 24 to deflect in two or more non-planar directions. In the illustrated embodiment shown in FIG. 2, the steerable catheter includes two pairs of steering wires 44 spaced approximately 90 degrees apart for providing 4-way steering (i.e., up/down/right/left) of the insertion shaft 24. In alternative embodiments, the steerable catheter includes two steering wires 44 that allow the user to steer the distal end in at least two non-planar directions.

The steering wires 44 are routed, for example, through a corresponding number of steering wire lumens of the insertion shaft 24. The lumens may be positioned within the wall of a tubularly configured shaft, defined by tubes extending through a central bore of the tubular shaft, or defined by bores 46 of an extruded shaft, as shown best in FIG. 2. The steering wires 44 preferably have sufficient tensile strength and modulus of elasticity so that they do not deform (elongate) during curved deflection. In one embodiment, the steering wires are made from 304 stainless steel with an 0.008 inch diameter and have a tensile strength of approximately 325 KPSI. The steering wires 44 may be lubricated or may be housed in a PTFE thin-walled extrusion (with or without lubricant) to help prevent the insertion shaft from binding up during deflection, if desired. The steering wires 44 may have any cross sectional geometry; in this embodiment they are round.

The distal ends of the steering wires 44 can be secured at the distal end 32 of the insertion shaft 24 in a conventional manner such that tension applied to the steering wires 44 causes the distal end 32 to deflect in a controllable manner. In embodiments having a discrete distal tip, the steering wires 44 may be anchored to the distal tip of the insertion shaft 24 using conventional techniques, such as adhesive bonding, heat bonding, crimping, laser welding, resistance welding, soldering, etc. In one embodiment, the steering wires 44 are attached via adhesive bonding, laser welding, resistance welding, soldering or other known techniques to a fluoroscopy marker band (not shown) fixedly attached to the distal tip 40 of the insertion shaft 24. The steering wires 44 extend from the distal end 32 of the insertion shaft 24 to the opposing, proximal end 30 of the insertion shaft 24 and terminate in a suitable manner at a steering system carried by the control handle 22, as will be described in detail below.

Returning to FIG. 1, the insertion shaft 24 is functionally connected at its proximal end 30 to the control handle 22. In the embodiment shown, the control handle 22 includes a handle housing 50 formed in one embodiment by two housing halves 50A-50B joined by appropriate removable fasteners, such as screws, or non removable fasteners, such as rivets, snaps, heat bonding, adhesive bonding, or interference fits (e.g., crush pins, etc.). In the embodiment shown, the proximal end 30 of the insertion shaft 24 is routed through a strain relief fitting 52 secured at the distal end of the handle housing 50. The handle housing 50 may include other features, if desired, such as one or more ports for providing access to optional channels of the insertion shaft 24. For example, the ports may include one or more of the following: an imaging device port 54; a working channel port 56; and an irrigation/suction port 58.

Figure 3:
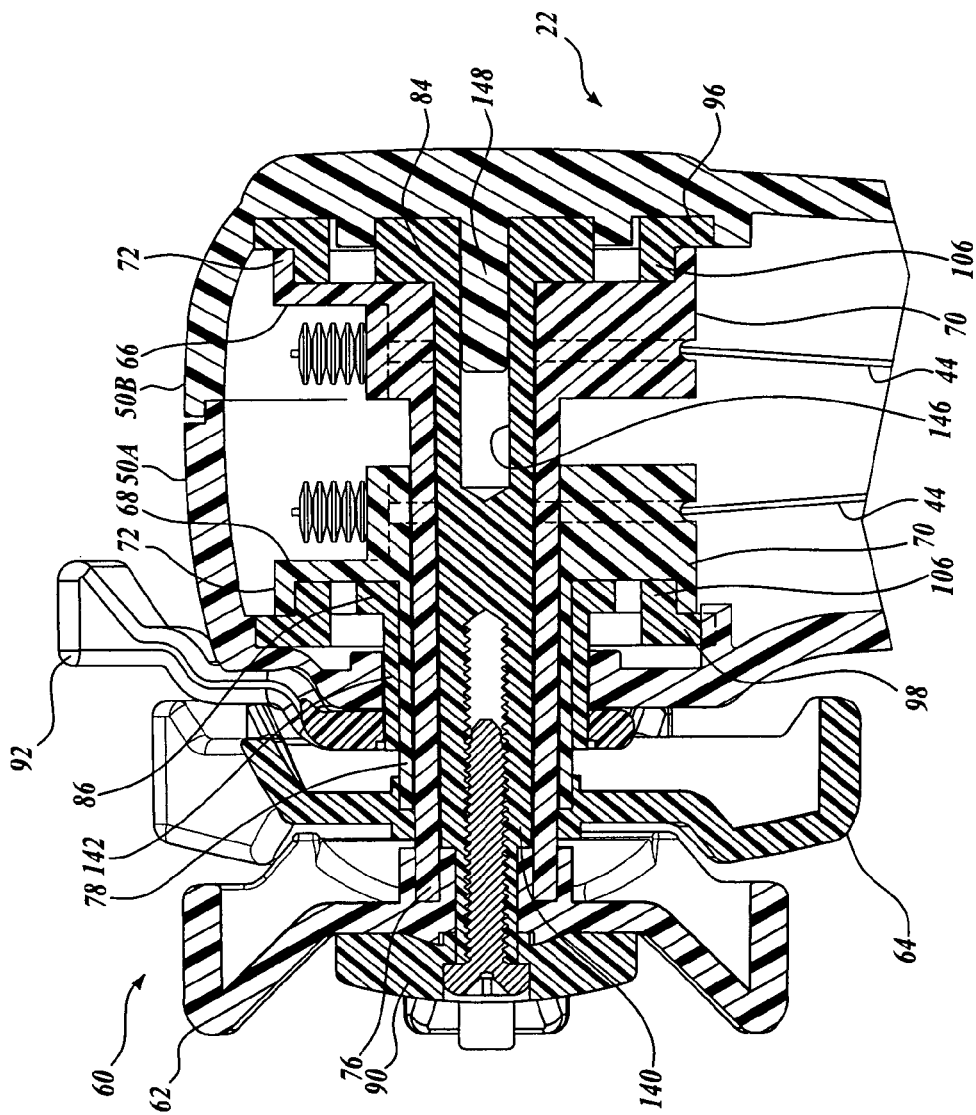
FIG. 3 is a partial cross sectional view of a control handle depicting one suitable embodiment of a steering system formed in accordance with aspects of the present invention.
Figure 4:
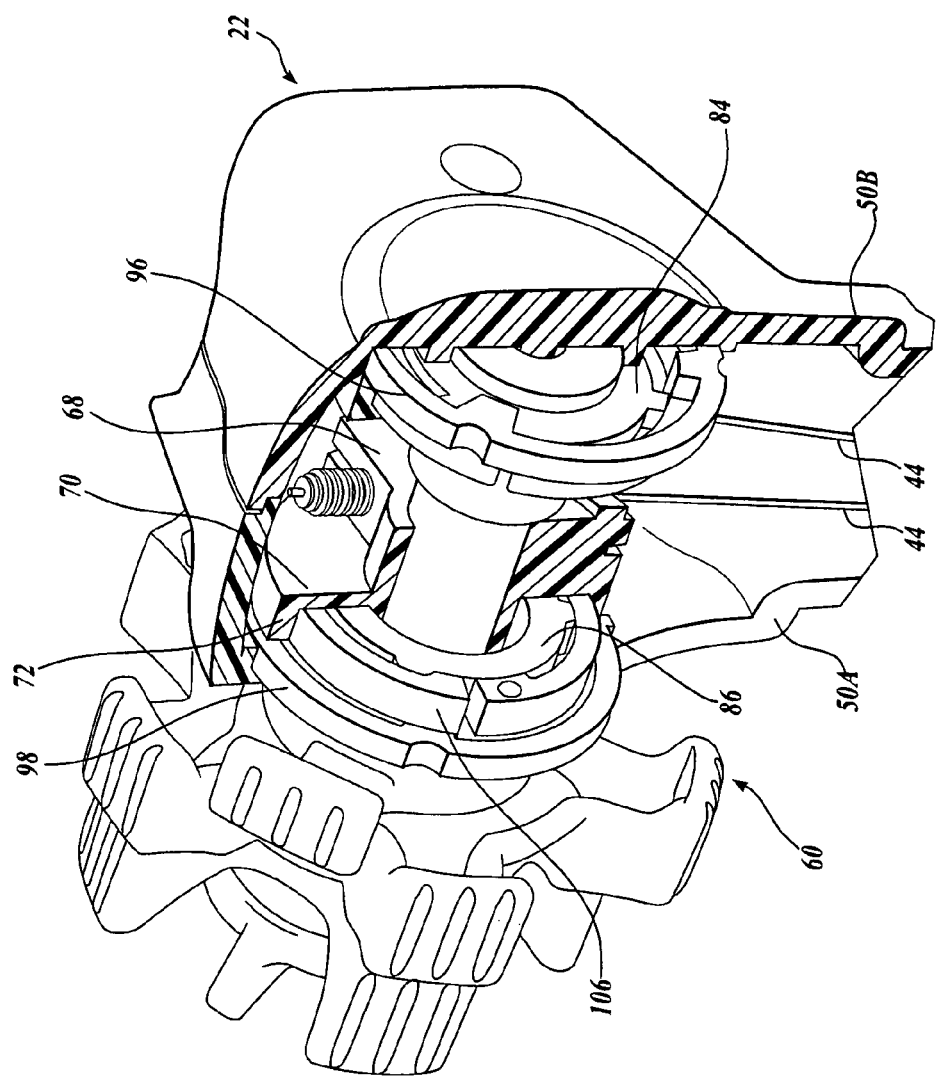
FIG. 4 is a partial perspective cut-away view of the control handle depicting the embodiment of the steering system shown in FIG. 3.
Figure 5:
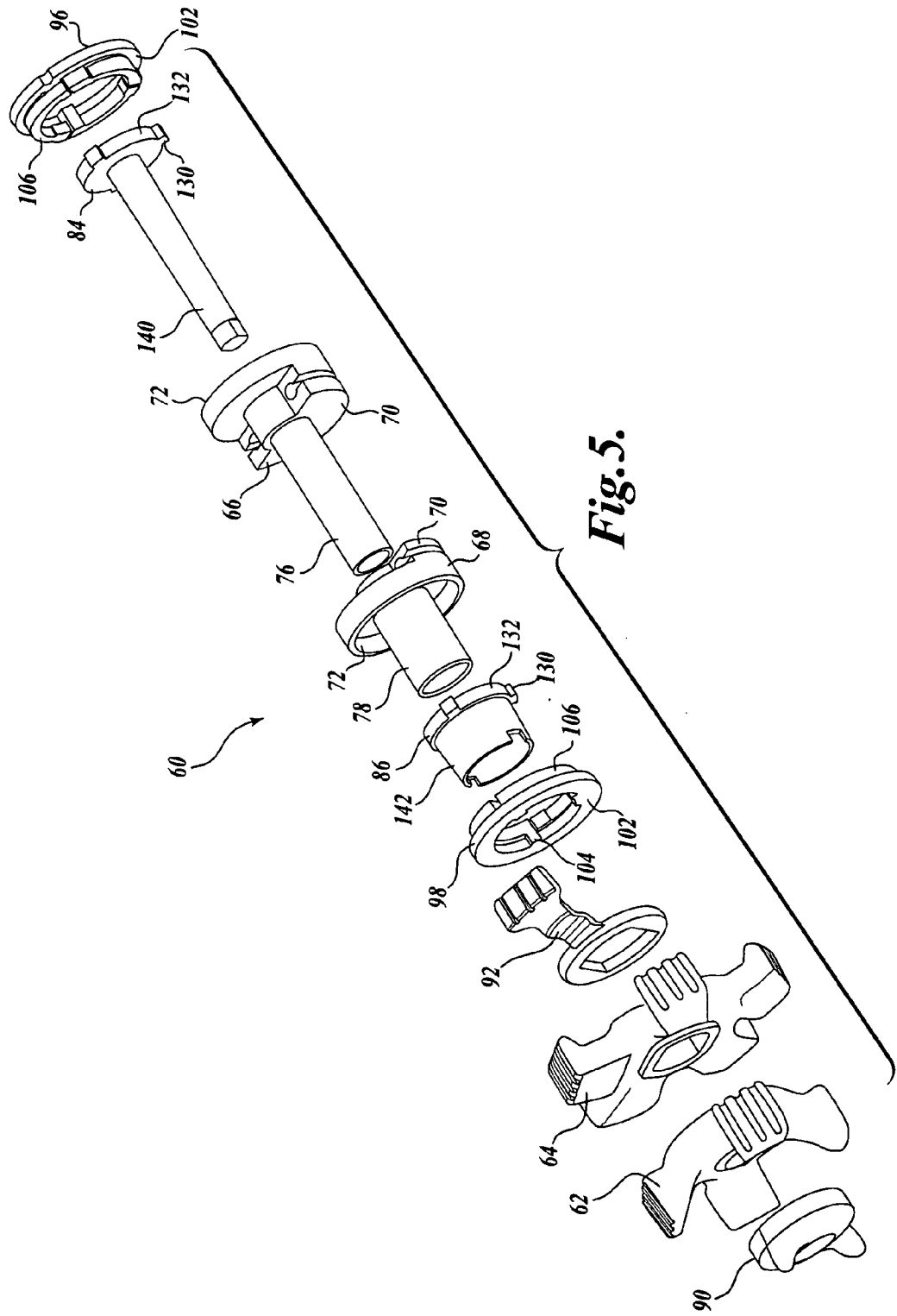
FIG. 5 is an exploded view of the steering system shown in FIG. 3.

As best shown in FIG. 3-5, the handle housing 50 carries one suitable embodiment of a steering system, generally designated 60, which is constructed in accordance with aspects of the present invention. In use, a physician or technician manually operates the steering system 60 for controlling the deflection of the distal end 32 of the insertion shaft 24 as the insertion shaft is advanced through vessels, passageways, etc., to an area of interest. Embodiments of the steering system 60 include two movable members that are operatively connected to the distal end of the insertion shaft via steering wires 44. In the embodiment shown, the movable members are control knobs 62 and 64, which are connected to two pairs of steering wires 44 for effecting 4-way steering of the distal end 32 of the insertion shaft 24 in the up/down direction and in the right/left direction. For example, the first control knob 62 is connected to a pair of steering wires 44 to control up/down steering and the second control knob 64 is connected to a pair of steering wires 44 to control right/left steering. Alternatively, other movable members may by employed, such as steering dials, linear sliders, etc., for steering the distal end of the insertion shaft 24. In other embodiments, a single steering wire 44 may be coupled to each of the movable members, such as the first and second control knobs 62 and 64. In these embodiments, it will be appreciated that the termination locations of the wires determine the directions in which the insertion shaft may deflect.

The steering system 60 further includes first and second drive members 66 and 68, which are interconnected between the first and second control knobs 62 and 64 and the pairs of steering wires 44. As best shown in FIG. 5, each drive member 66 and 68 is an integrally formed piece of material, such as plastic, defining a truncated or semi-circular pulley 70 on one side and an outwardly extending rim 72 on the other. While in the embodiment shown the rim 72 forms a hollow cylinder, the rim 72 may be alternatively configured with one of more spaced apart arcuate sections. As will be described in detail below, the rim 72 functions like a brake drum defining one or more braking surfaces against which portions of the locking mechanism act to arrest or partially arrest rotation of the drive members.

Still referring to FIGS. 3-5, the first drive member 66 can be integrally formed or keyed for rotation with one end of a cylindrical drive shaft 76. The other end of the drive shaft 76 can be keyed or otherwise attached to the first control knob 62 for co-rotation. Likewise, the second drive member 68 can be integrally formed or keyed for rotation with one end of a second cylindrical drive shaft 78. The other end of the drive shaft 78 can be keyed or otherwise attached to the second control knob 64 for co-rotation. When assembled, the proximal ends of a first pair of steering wires 44 can be secured to opposite sides of the pulley 70 of the first drive member 66 in a conventional manner. Likewise, the proximal ends of a second pair of steering wires 44 are secured to opposite sides of the pulley 70 of the second drive member 68 in a conventional manner. As a result, rotation of the control knobs 62 and 64 rotates the drive members 66 and 68, which in turn, applies tension to the steering wires 44 for deflecting the distal end of the insertion shaft 24 to a desired deflection angle.

In accordance with aspects of the present invention, the steering system 60 may further include a locking mechanism that functions to lock or partially lock the distal end of the insertion shaft 24 in a desired deflection position or angular attitude during use. For example, several embodiments of the locking mechanism can be configured to lock the position of the distal end of the insertion shaft in a first direction independently of movement of the distal end in a second non-planar direction. Stated differently, several embodiments of the locking mechanism can be configured to arrest the movement of the distal end of the insertion shaft in one direction while allowing it to move in a second non-planar direction. This may be desirable for providing more operator control to effect the desired angular attitude of the distal end for proper guidance through the vessel, passageway, etc.

This can be accomplished by, for example, arresting the movement of the first and/or second control knobs 62 and 64, by arresting the movement of the first and/or second drive members 66 and 68, or arresting the movement of the first and/or second pairs of steering wires 44 associated with the control knobs 62 and 64. As will be described in detail below, one embodiment of the locking mechanism shown in FIGS. 1 and 3-7B arrests the movement of the first and second drive members 66 and 68 by, for example, impeding the rotation thereof. However, other techniques of arresting the movement of the control knobs, the drive member, the steering wires, or combinations thereof are contemplated to be within the scope of the present invention, as defined by the claims.

Thus, by arresting the movement of the drive members 66 and 68 independently, the distal end of the insertion shaft can be locked from movement in one direction while allowing continued deflection of the distal end of the insertion shaft in a second non-planar direction. As will be described in detail below, embodiments of the lock mechanism may apply resistive forces for partially locking the position of the distal end of the insertion in one or more non-planar directions.

Referring now to FIGS. 3-7B, one embodiment of the locking mechanism suitable for use in the steering system 60 will be described in detail. As best shown in FIG. 3-6, the locking mechanism comprises first and second locking devices. The first and second locking devices comprise first and second cam members 84 and 86, first and second lock members, such as lock levers 90 and 92, and first and second brake members 96 and 98, respectively. The first and second brake members 96 and 98 and the first and second cam members 84 and 86 cooperatively function via movement of the first and second lock levers 90 and 92, respectively, to restrict movement, i.e., rotation, of the first and second drive members 66 and 68.

Figure 6:
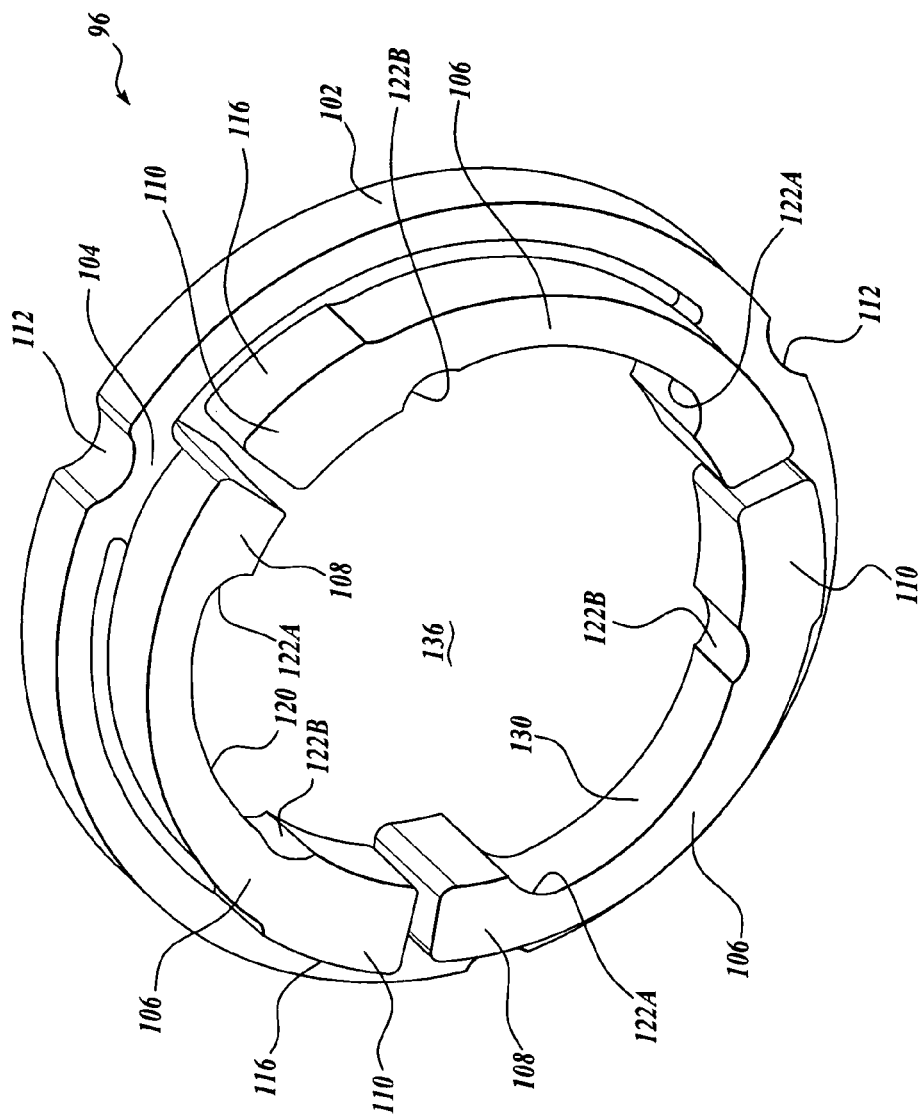
FIG. 6 is a perspective view of one embodiment of a brake member constructed in accordance with aspects of the present invention.

As best shown in FIGS. 5 and 6, the brake members 96 and 98 each comprise a generally circular ring 102 as its base having one or more inwardly projecting tabs 104 spaced around the inner perimeter thereof. The brake members 96 and 98 further include one or more brake arms 106 that are attached at one end to the top surface of a respective tab 104 and extend in a cantilevered manner to a free end 110. In the embodiment shown in FIG. 6, the one or more brake arms 106 include three brake arms, which are positioned in a plane parallel to and adjacent the ring 102. The brake arms 106 extend around the ring in manner shown in FIG. 6.

The brake members 96 and 98 are constructed from a suitable material or combination of materials, such as plastic or various metals, which allows the cantilevered brake arms 106 to flex outwardly for interaction with the inner rim 72 when force is applied and to return to their unflexed position upon removal of the applied force. The ring 102 further includes notches 112 around its perimeter for interfacing with structure within the handle housing for preventing rotation of the brake member when assembled.

As best shown in FIG. 6, each brake arm 106 defines a braking surface 116 at the exterior surface of the free end 110. In the embodiment shown, the brake surfaces 116 are configured with a convex geometry for cooperating with the inner surface of the rim 72. The braking surfaces 116 may be textured, coated with high fiction materials, etc., to enhance the braking effect. The brake arms 106 further define cam surfaces 120 along their interior surfaces. The cam surfaces 120 are configured with a geometry such that as the cam surfaces extend from the fixed end 108 of the brake arms 106 to a position in proximity of the free end 110, the cam surface 120 gradually progresses radially inwardly to the center of the cavity 136. It will be appreciated that the number of brake arms 106, the size and geometry of the cam surfaces and brake surfaces, etc., can vary to effect more or less braking force, depending, for example, on the intended application.

Figure 8:
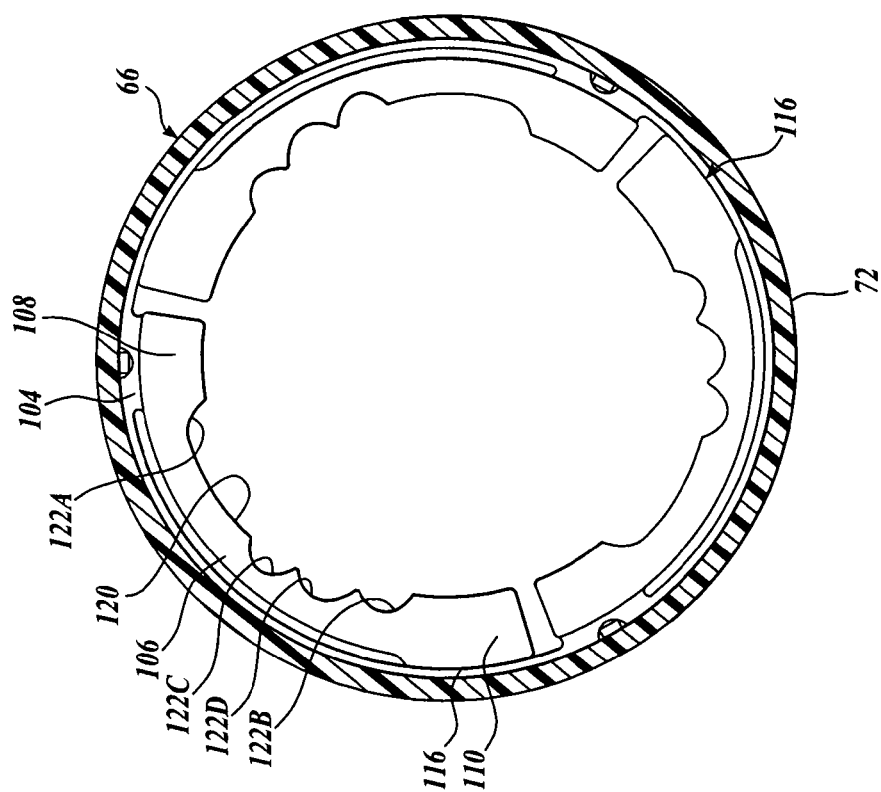
FIG. 8 is a top view of an alternative embodiment of the brake member housed within a drive member.

Referring to FIG. 6, the beginning and ending of the cam surfaces 120 can be formed with detent notches 122A and 122B, respectively, which cooperate with a portion of the cam member for providing indexed movement between locked and unlocked positions. In an alternative embodiment shown in FIG. 8, one or more detent notches 122C, 122D, etc., can be formed in the cam surfaces 120 between the detent notches 122A and 122B for providing one or more partial locking positions that apply varying (e.g., increasing) braking forces to the drive members. This allows the drive members to rotate against a selected resistance, which may aid, for example, in precision steering of the distal end. As such, the locking member can move from the unlocked position to one or more of the partial locking positions, which applies a partial braking force (i.e., one that resists rotation of the drive member), or to the locked position, also referred to as the fully locked position, which applies a full braking force (i.e., one that prohibits rotation) on the drive member.

Referring now to FIGS. 5, 6 and 7A-B, each cam member 84 and 86 can include a plurality of cams 130 for interacting with the cam surfaces 120 of the brake members 96 and 98. It will be appreciated that the number of cams 130 corresponds to the number of brake arms 106. In the embodiment shown, the cam members 84 and 86 each comprise a cylindrical hub 132 from which the cams 130 outwardly extend. The cam members 84 and 86 are cooperatively sized to be rotatingly received within the cavity 136 defined by the brake members 96 and 98 such that the cams 130 contact the cam surfaces 120 in the manner shown in FIGS. 7A-7B.

As best shown in FIGS. 4 and 6, the first cam member 84 can be integrally formed or keyed for rotation with one end of a cylindrical drive shaft 140. The other end of the drive shaft 140 can be keyed or otherwise attached to the first lock lever 90 for co-rotation. Similarly, the second cam member 86 can be integrally formed or keyed for rotation with one end of a cylindrical drive shaft 142. The other end of the drive shaft 142 can be keyed or otherwise attached to the second lock lever 92 for co-rotation. As a result, rotation of the first and second lock levers 90 and 92 can rotate the first and second cam members 84 and 86 within the first and second brake members 96 and 98, respectively, thereby causing the cams 130 of the first and second cam members 84 and 86 to interact with the brake arms 106 of the first and second brake members 96 and 98.

Turning now to FIG. 3, the steering system 60 is shown in its assembled state for operation by a user to selectively deflect the distal end of the insertion shaft, and to lock the distal end against movement in one or more directions. As assembled, the first brake member 96 is mounted in a non-rotational manner to structure of the housing half 50B. The first cam member 84 is rotationally supported within the housing via its inner bore 146, which receives a fixed shaft 148 integrally formed or otherwise positioned to extend into the interior of the housing half 50B. When rotationally supported in the housing, the first cam member 84 is received within the cavity of the first brake member 96 and cooperates therewith such that the cams of the first cam member 84 interface with the cam surfaces of the brake arms 106.

Continuing to described the assembled state of the steering system 60, the first drive member 66 is rotationally supported over the drive shaft 140 of the cam member 84 for independent rotation with respect to the first cam member 84. The first drive member 66 can be positioned such that its rim 72 extends around the perimeter of the brake arms 106. The second drive member 68 is rotationally supported over the drive shaft 76 of the first drive member 66 for independent rotation with respect to the first drive member 66. As assembled, the first drive member 66 should be spaced apart from the second drive member 68 so that one does not interfere with rotation of the other.

The second cam member 86 can be rotationally supported over the drive shaft 78 of the second drive member 68 for independent rotation with respect to the second drive member 78. Similar to the first brake member 96, the second brake member 98 can be mounted in a non-rotational manner to structure of the housing half 50A. When rotationally supported in the housing by the drive shaft 78, the second cam member 86 can be received within the cavity of the second brake member 98 and cooperates therewith such that the cams of the second cam member 86 interface with the cam surfaces of the brake arms 106. The second drive member 68 can be further positioned such that its rim 72 extends around the perimeter of the brake arms 106 of the second brake member 68.

Still referring to FIG. 3, the ends of the drive shafts 76, 78, 140, and 142 associated with the first drive member 66, the second drive member 68, the first cam member 84, and the second cam member 86, respectively, extend through an opening in the housing half 50A in a rotationally supported manner and outwardly of the housing half 50A. The first control knob 62, the second control knob 64, the first lock lever 90 and the second lock lever 92 are attached in a suitable manner to the drive shafts 76, 78, 140, and 142, respectively, for co-rotation.

One method of operating an embodiment of the steerable catheter 20 will now be described with reference to FIGS. 1-7B. First, the operator inserts the insertion shaft 24 into a conduit with the lock levers 90 and 92 in the unlocked positions. As the operator advances the insertion shaft 24 into the conduit, vessel, passageway, body lumen, etc., the operator can manipulate the first and second control knobs 62 and 64 independently to "steer" the distal end 32 of the insertion shaft 24 to the area of interest. When the operator wishes to lock the distal end 32 from deflective movement in one direction, while allowing the distal end 32 to deflect in another non-planar direction, the operator can activate the lock lever corresponding to the drive member that effects steering in that specific direction. For example, if the operation wishes to lock the distal end 32 from deflective movement in the up or down direction, the operator can move the lock lever 90 from its unlocked position to its locked position.

By moving the lock lever 90 from the unlocked position to the locked position, the cam member 84 associated with the lock lever 90 can move from the unlocked position shown in FIG. 7A to the locked position shown in FIG. 7B. In the unlocked position of FIG. 7A, the cams 130 are positioned within the notches 122A at the beginning of the cam surfaces 120, and the brake surfaces 116 of the brake arms 106 are free from engagement with the rim 72 of the drive member 66. When the cam member 84 rotates in the direction of the arrow to the position shown in FIG. 7B, the cams 130 follow the cam surfaces 120 of the brake arms 106 to the notches 122B at the end of the cam surfaces 120. Due to the configuration of the cam surfaces 120, the cams 130 force the brake arms 106 outwardly in such a manner that the brake surfaces 116 of the brake arms 106 frictionally engage the rim 72 of the drive member 66, thereby arresting rotation of the drive member 66.

In the locked position of FIG. 7B, the drive member 66 is precluded from rotation, which in turn, precludes movement of the distal end 32 of the insertion shaft 24 in the up/down direction. The distal end 32, however, is still free to move, i.e., deflect, in the left/right direction by rotation of control knob 64. If the operator wishes the lock the distal end 32 from deflective movement in the right or left direction, the operator can then move the lock lever 92, which is associated with the cam member 86 and drive member 68, from the unlocked position to the locked position.

If the operator subsequently desires to continue steering the distal end 32 of the insertion shaft 24 by changing the deflection angle of the distal end 32 from its current position to another position, one or both of the lock levers 90, 92 can be moved from the locked position to the unlocked position. This, in turn, rotates the cam members with respect to the drive members. Again, due to the configuration of the cam surfaces 120 of the brake arms 106, and the flexure thereof, the brake surfaces 116 of the brake arms 106 are removed from contact with the rims 72 of the brake members. This alleviates the friction between the brake surfaces 116 of the brake arms 106 and the rims 72 of the drive members 66 and 68, thereby allowing the first and second drive members 66 and 68 to rotate by turning the control knobs 62 and 64.

Embodiments of the locking mechanism thus far have been shown and described to include two substantially similar locking devices (i.e., locking member/cam member/brake member) to arrest or partially arrest the movement of the drive members. It will be appreciated that embodiments of the locking mechanism need not be so limiting. For example, alternative embodiments of the locking mechanism may employ other locking devices, including conventional or future developed locking devices, for arresting or partially arresting one or both of the drive members 66 and 68.

Other locking devices that may be practiced with embodiments of the locking mechanism, and thus, are within the scope of the present invention, as claimed, may include but are not limited to set screws, sliding pins, or the like, which are appropriately carried by the handle housing 50. In several embodiments, the set screw or sliding pin can be configured and arranged for selectively engaging a portion of an associated drive member. For example, the set screw or sliding pin may engage a threaded or non-threaded bore or like structure disposed in the associated drive member or may abut against a cooperating side face of the truncated pulley (acting as a rotational stop) for prohibiting movement (e.g., rotation) of the drive member.

In other embodiments, the end of the set screw may apply a braking force against a face of the drive member for arresting or partially arresting the movement of the drive member. It will be appreciated that the end of the set screw may be configured with an end surface that is larger than its threaded shaft, and may include texturing, friction coating, etc., to enhance the applied braking force. Of course, the locking mechanism can employ any combination of the locking devices described herein or known or future developed locking devices for arresting or partially arresting the control knobs, the drive members, the steering wires, or combinations thereof.

While illustrative embodiments have been illustrated and described, it will be appreciated that various changes can be made therein without departing from the spirit and scope of the invention, as claimed. For example, while embodiments of the steering system have been described as not including steering wires, it will be appreciated that steering wires may be included in the steering systems of the present invention.

The invention claimed is:

1. A steering system for a steerable device having a deflectable insertion shaft through which at least first and second steering wires are routed, the steering system comprising:
    first and second drive members having an axis of rotation and adapted to be coupled to the first and second steering wires for effecting movement of the first and second steering wires, respectively;
    a first lock member associated with the first drive member, the first lock member moveable between an unlocked position, wherein the first drive member is freely movable to effect movement on the first steering wire, and a locked position, wherein the first drive member is prohibited from effecting movement on the first steering wire; and
    a second lock member associated with the second drive member and movable independently of the first lock member, the second lock member movable between an unlocked position, wherein the second drive member is movable to effect movement on the second steering wire, and a locked position, wherein the second drive member is prohibited from effecting a movement on the second steering wire;
    wherein the first lock member includes a first brake arm configured to deflect radially outwardly relative to the axis of rotation when the first lock member is moved to lock the first drive member; and
    wherein a frictional engagement between a radially outward facing surface of the first brake arm and a radially inward facing surface of the first drive member causes a radially directed force sufficient to arrest movement of the first drive member, further comprising a first cam member having a first cam configured to engage with a first notch on the first brake arm, wherein rotation of the first cam member causes the first brake arm to deflect radially outward.

2. The steering system of claim 1, further comprising first and second levers coupled for co-action with the first and second drive members, respectively.

3. The steering system of claim 2, wherein the first and second levers are control knobs.

4. The steering system of claim 1, further comprising first and second brake members configured to respectively prohibit the first and second drive members from effecting movement of the first and second steering wires.

5. The steering system of claim 4, further including a second cam member connected for co-action with the second lock member, the first and second cam members interacting with the first and second brake members, respectively, for prohibiting the first and second drive members from effecting movement of the first and second steering wires.

6. The steering system of claim 5, wherein the first brake member includes the first brake arm and the second brake member includes a second brake arm configured to deflect radially outwardly relative to the axis of rotation when the second lock member is moved to lock the second drive member and having a radially outward facing surface, wherein the radially outward facing surface of each of the first and second brake arms is configured to move into engagement with a respective one of the first radially inward facing surface of the first drive member and a second radially inward facing surface of the second drive member when interacting with the first and second cam members, respectively.

7. The steering system of claim 6, wherein each of the first and second lock members includes at least three brake arms configured to deflect radially outwardly relative to the axis of rotation.

8. The steering system of claim 1, wherein at least one of the first and second lock members are lock levers or a portion of a brake member.

9. The steering system of claim 1, wherein movement of the first and second lock members cause contact against a respective one of the first and second drive members in a manner sufficient to arrest movement thereof.

10. The steering system of claim 6, wherein each of the first and second brake arms defines a cam surface, and wherein the second cam member includes a cam that corresponds with the second brake arm and interfaces with the cam surface of the second brake arm.

11. The steering system of claim 10, wherein movement of the first and second cam members cause the cams to follow the cam surfaces, thereby forcing the radially outward facing surfaces of the first and second brake arms into contact with a respective one of the radially inward facing surfaces of the first and second drive members.

12. The steering system of claim 11, wherein each of the cam surfaces includes a notch located at the ends of the cam surfaces, the notches being associated with an unlocked and a locked position of a respective one of the first and second drive members.

13. The steering system of claim 12, wherein each of the cam surfaces includes one or more notches between the ends of the cam surfaces, the one or more notches being associated with one or more partially locked positions of a respective one of the first and second drive members.

14. A steering system for a steerable device, comprising:
    first and second steering wires;
    first and second drive members having an axis of rotation and coupled to the first and second steering wires for selectively tensioning the first and second steering wires, respectively;
    first and second lock members independently movable between unlocked positions, wherein the first and second steering wires are freely movable, and one or more positions that either restrict or resist movement of the first and second steering wires;
    wherein the first lock member includes a first brake arm configured to deflect radially outwardly relative to the axis of rotation when the first lock member is moved to lock the first drive member; and
    wherein a frictional engagement between a radially outward facing surface of the first brake arm and a radially inward facing surface of the first drive member causes a radially directed force sufficient to arrest movement of the first drive member, further comprising a first cam member having a first cam configured to engage with a first notch on the first brake arm, wherein rotation of the first cam member causes the first brake arm to deflect radially outward.

15. The steering system of claim 14, wherein the movement of at least one of the first and second lock members is indexed.

16. The steering system of claim 14, wherein one of the one or more positions is selected from a group consisting of a locked position, wherein movement of the associated steering wire is restricted, and a partially locked position, wherein movement of the associated steering wire is resisted.

17. A control handle of a steering device, the control handle comprising:
a handle housing adapted for connection to a deflectable insertion shaft through which at least first and second steering wires are routed;
a steering system carried by the handle housing, the steering system comprising:
first and second drive members adapted for connection to the ends of the first and second steering wires and having an axis of rotation;
a locking mechanism that locks the movement of the first drive member independently of the second drive member and locks the movement of the second drive member independently of the first drive member, wherein the locking mechanism includes a first brake arm configured to deflect radially outwardly relative to the axis of rotation when the locking mechanism is moved to lock the first drive member; and wherein a frictional engagement between a radially outward facing surface of the first brake arm and a radially inward facing surface of the first drive member causes a radially directed force sufficient to arrest movement of the first drive member; and
a first cam member having a first cam configured to engage with a first notch on the first brake arm, wherein rotation of the first cam member causes the first brake arm to deflect radially outward.

18. The control handle of claim 17, wherein the locking mechanism includes first and second locking members configured to engage with the first and second drive members, respectively.

19. A steerable device, comprising:
an elongated shaft having proximal and distal ends, and a deflectable distal region;
a control handle functionally coupled to the proximal end of the elongated shaft;
a steering system having an axis of rotation, carried by the control handle, and coupled to the distal end of the elongated shaft for deflecting the distal end about the deflectable distal region in at least first and second non-planar directions;
first and second drive members rotatably mounted about the axis of rotation; and
a locking mechanism that locks the distal end of the elongated shaft against movement in the first direction independently of locking the distal end of the elongated shaft against movement in the second direction, wherein the locking mechanism includes a first brake arm configured to deflect radially outwardly relative to the axis of rotation when the locking mechanism is moved to lock the first drive member; and
wherein a frictional engagement between a radially outward facing surface of the first brake arm and a radially inward facing surface of the first drive member causes a radially directed force sufficient to arrest movement of the first drive member, further comprising a first cam member having a first cam configured to engage with a first notch on the first brake arm, wherein rotation of the first cam member causes the first brake arm to deflect radially outward.

20. The steerable device of claim 19, wherein the first and second drive members of the steering system are movably mounted to the control handle, and at least first and second steering wires are routed through the elongated shaft and coupled between the first and second drive members and the distal end of the elongated shaft.

21. The steerable device of claim 20, wherein each of the first and second drive members are rotationally mounted about the axis of rotation, and wherein the steering system further includes first and second control knobs connected to the first and second drive members, respectively, for co-rotation.

22. The steerable device of claim 20, wherein the locking mechanism includes a first lever movable between an unlocked position and a locked position, a first brake member, and the first cam member being cooperatively associated with the first brake member such that movement of the first lever from the unlocked position to the locked position causes the first cam member to force the radially outward facing surface of the first brake member into abutment against the radially inward facing surface of the first drive member.

23. The steerable device of claim 22, wherein the locking mechanism further includes a second lever having a radially outward facing surface and movable between an unlocked position and a locked position, a second brake member configured to deflect radially outwardly relative to the axis of rotation when the locking mechanism is moved to lock at least the second drive member having a radially inward facing surface, and a second cam member cooperatively associated with the second brake member such that movement of the second lever from the unlocked position to the locked position causes the second cam member to force a radially outward facing surface of the second brake member into abutment against the radially inward facing surface of the second drive member.

24. The steerable device of claim 19, further including first and second pairs of steering wires routed through the elongated shaft, the ends of which terminate at the distal end of the elongated shaft in a manner as to effect 4-way steering of the distal end of the elongated shaft;
wherein the first and second drive members are rotatably supported about the axis of rotation by the control handle and coupled to the proximal ends of first and second pairs of the steering wires, respectively, and further including first and second control knobs coupled for co-rotation with the first and second drive members respectively, wherein rotation of the control knobs effect 4-way steering of the distal end of the elongated shaft.

25. A steerable device, comprising:
an elongated shaft having proximal and distal ends, and a deflectable distal region;
a control handle functionally coupled to the proximal end of the elongated shaft;
a steering system having an axis of rotation and including first and second drive members rotatably mounted about the axis of rotation, carried by the control handle, and coupled to the distal end of the elongated shaft for deflecting the distal end about the deflectable distal region in at least first and second non planar directions; and
a locking mechanism configured to prohibit movement of the distal end of the elongated shaft in the first direction while allowing continued deflection of the distal end of the elongated shaft in the second direction, wherein the locking mechanism includes a first brake arm configured to deflect radially outwardly relative to the axis of rotation when the locking mechanism is moved to lock the first drive member;

wherein a frictional engagement between a radially outward facing surface of the first brake arm and a radially inward facing surface of the first drive member causes a radially directed force sufficient to arrest movement of the first drive member; and a first cam member having a first cam configured to engage with a first notch on the first brake arm, wherein rotation of the first cam member causes the first brake arm to deflect radially outward.

\* \* \* \* \*

UNITED STATES PATENT AND TRADEMARK OFFICE
CERTIFICATE OF CORRECTION

| | | |
|---|---|---|
| PATENT NO. | : 8,641,604 B2 | Page 1 of 1 |
| APPLICATION NO. | : 12/464770 | |
| DATED | : February 4, 2014 | |
| INVENTOR(S) | : Golden et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 615 days.

Signed and Sealed this
Eighteenth Day of August, 2015

Michelle K. Lee
*Director of the United States Patent and Trademark Office*